United States Patent [19]

van Hout et al.

[11] Patent Number: 5,399,657
[45] Date of Patent: Mar. 21, 1995

[54] METHOD OF PREPARING CHLOROFORMATE COMPOUNDS

[75] Inventors: Henricus H. M. van Hout, Halsteren; Christianus J. J. Maas, Rilland; Laurus van der Wekke; Martin H. Oyevaar, both of Goes, all of Netherlands

[73] Assignee: General Electric Company, N.Y.

[21] Appl. No.: 142,737

[22] Filed: Oct. 26, 1993

[30] Foreign Application Priority Data

Oct. 27, 1992 [NL] Netherlands ............ 9201859

[51] Int. Cl.$^6$ ............................ C08G 64/00
[52] U.S. Cl. ........................ 528/198; 558/282
[58] Field of Search ............ 558/282; 528/198

[56] References Cited

U.S. PATENT DOCUMENTS

| 4,638,077 | 1/1987 | Brunelle et al. | 558/282 |
| 4,816,420 | 3/1989 | Brunelle et al. | 528/198 |
| 4,864,011 | 9/1989 | Bussink et al. | 528/198 |

FOREIGN PATENT DOCUMENTS

| 1117598 | 1/1960 | Germany . |
| 1200768 | 8/1970 | United Kingdom . |

*Primary Examiner*—John Kight, III
*Assistant Examiner*—Terressa Mosley

[57] ABSTRACT

The invention relates to a method of preparing a compound of formula 1

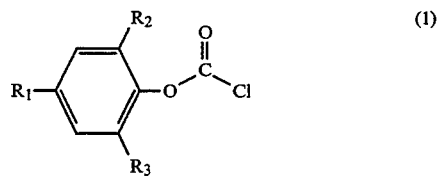

wherein $R_1$, $R_2$ and $R_3$ correspond to H, a branched or non-branched, optionally substituted alkyl group, or an optionally substituted aryl group, suitable as a chain stopper in the preparation of an aromatic polycarbonate, by reaction of a compound of formula 2

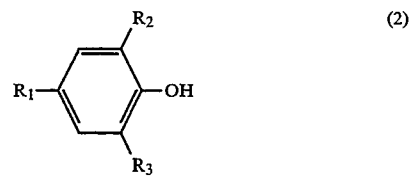

wherein $R_1$, $R_2$ and $R_3$ have the meanings described hereinbefore, with phosgene, comprising the continuous supply of the compound of formula 2 and phosgene to a solution of phosgene in a solvent, the temperature being kept at a value between 0° and 15° C. and the pH being kept at a value between 1 and 6.

8 Claims, No Drawings

METHOD OF PREPARING CHLOROFORMATE COMPOUNDS

The present invention relates to a method of preparing chloroformate compounds of the formula:

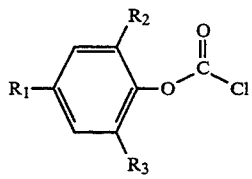

wherein $R_1$, $R_2$ and $R_3$ correspond to H, a branched or non-branched, optionally substituted alkyl group, or an optionally-substituted aryl group. Such compounds are suitable more in particular as chain stoppers in the preparation of aromatic polycarbonates.

This use is described inter alia in U.S. Pat. No. 4,864,011. It has been found that the conventional methods of preparing chloroformates by reaction of phosgene and a phenolic component may give rise to the formation of undesired reaction products, for example, dimers. The presence of these reaction products, for example, diphenyl carbonates, in the chain stopper is undesired. As a matter of fact, the use of a chain stopper comprising dimer would result in the ultimate polycarbonate ultimately also comprising dimer. This dimer has a comparatively low melting-point and will melt sooner during the processing of the polycarbonate, and will exude. The vapour of the dimer will condense on the matrix and will give rise to surface defects.

A possible solution to this problem is a complementary purification of the chloroformate. However, such purifications are expensive, so that the use of the ultimate chain stopper often is not justified economically.

Therefore, there exists a need for a method of preparing phenyl chloroformates, in which so few by-products are formed already during the preparation that complementary purification is not necessary. The invention therefore relates to a method of preparing a compound of formula 1

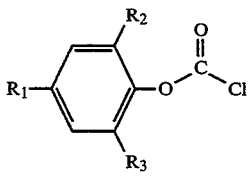

wherein $R_1$, $R_2$ and $R_3$ correspond to H, a branched or non-branched, optionally substituted alkyl group, or an optionally substituted aryl group suitable as a chain stopper in the preparation of an aromatic polycarbonate, by reaction of a compound of formula 2

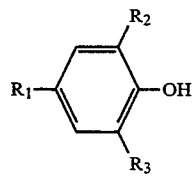

wherein $R_1$, $R_2$ and $R_3$ have the meanings described hereinbefore, with phosgene, comprising the continuous supply of the compound of formula 2 to a solution of phosgene in a solvent, the temperature being kept at a value between 0° and 40° C. and the pH being kept at a value between 1 and 6.

It has been found surprisingly that, when using the present method, the final product consists of a solution of the desired phenyl chloroformate in an organic solvent, the content of by-products being so low that either the solution as such may be used as a chain stopper, or the phenylchloroformate may immediately be used after separation from the solution. In the cases in which an extremely high purity is desired, the phenyl chloroformate may still be subjected to a complementary purification.

It is to be noted that a method of preparing chloroformate compositions is known from U.S. Pat. No. 4,638,077. This Patent Specification is mainly directed to the preparation of compounds starting from bisphenol A, i.e. difunctional compounds. As appears from the specification it is endeavoured to obtain compositions which mainly comprise monomeric, dimeric and trimeric compounds, while, as appears from column 2, lines 17-20, at most 90% is converted into monomeric compounds. This means that at least 10% of the composition consists of the undesired components. According to the invention the content of dimeric compounds comprises at most 5,000 ppm, which corresponds to at most 0.5%. According to preferred embodiments of the invention, however, considerably lower contents of the undesired diaryl carbonates may be obtained.

According to the invention, various phenyl chloroform ate compounds can be prepared. Depending on the choice of the substituents $R_1$, $R_2$ and $R_3$, for example, phenyl chloroform ate, tertiary butyl phenyl chloroform ate, octyl- or nonylphenyl chloroform ate, paracumyl phenyl chloroform ate and other substituted phenyl chloroformates may be obtained when used as a chain stopper, the nature of the polycarbonate to be prepared mainly determines the choice of the substituent.

The method according to the invention is first of all characterised in that a solution of phosgene in a solvent is provided at low temperature in a reactor, to which solution phosgene and a phenol compound are then added, the temperature and the pH being kept at the desired values. After termination of the dosing of the phenolic compound the reaction mixture is allowed to react for some more time. This is preferably done at least partly with complementary supply of phosgene. It is to be noted that the molar ratio phosgene/phenolic compound is preferably larger than 1:1, which implies that excess of phosgene is present. The said excess on a molar basis is preferably 1.5:1 to 3:1.

It is of great importance for the temperature to be at a value between 0° and 40° C. during the reaction, preferably between 0° and 15° C. and more preferably between 5° and 15° C. The pH of the reaction mixture is also of importance. It should be kept low, but again it should not be kept too low. Therefore, NaOH or another basic compound will generally be dosed during the reaction so as to keep the pH at the correct value. The best suitable pH value during dosing the phenolic compound also depends on the nature of the phenolic compound. If phenol is used, the pH should preferably be kept at a value between 1 and 4, while in the case of paracumyl phenol the said value is between 4 and 6.

In connection with the dosing of a basic compound it should be ensured that the amount of water is at least such that saturation with electrolyte does not occur. Since chloride is released during the reaction, the formation of sodium chloride occurs with the addition of sodium hydroxide solution. The amount of water should hence be so high that the sodium chloride remains in solution. It is to be noted that a quantity of water is preferably present in the reaction mixture to initiate the reaction between phosgene and the phenolic compound. This quantity of water may be restricted to the quantity which is necessary for the initiation and it will in general be between 5 and 25% by weight of the quantity of organic solvent. This organic solvent may be chosen from the group consisting of dichloromethane and monocholorobenzene. Dichloroethane is preferably used, since it has been found that herewith the best results are obtained.

As already indicated, the solution of phenyl chloroformate in the organic solvent obtained according to the method of the present invention may directly be used in the preparation of aromatic polycarbonates. The invention therefore also relates to a solution of the compound of formula 1 in an organic solvent, and the use thereof as a chain stopper in the preparation of polycarbonate.

The invention also relates to a method of preparing polycarbonate, comprising the reaction of a carbonate precursor with a diphenol in the presence of the chain stopper obtained while using the method according to the invention. An example of such a preparation of polycarbonate is described in U.S. Pat. No. 4,864,011, the contents of which Patent Specification are incorporated herein by reference.

The invention will now be described in greater detail with reference to a few examples which are not to be deemed as constituting any restriction of the present invention.

EXAMPLE 1

Phenyl chloroformate was prepared in a stirred reactor at a temperature which was kept below 10° C. by cooling. 1320 ml of methylene chloride were provided in the reactor together with 150 ml of water. 7.4 g/minute of phosgene were dosed for 10 minutes. 70.5 g of phenol in 333 ml of methylene chloride were then dosed in the course of 35 minutes. During this dosing of phenol, 3.7 g/min. of phosgene were added. The pH was kept at a value of 2–4 by dosing with sodium hydroxide solution. During the dosing of phenol 30 ml of water were added four times to the reactor. After termination of the phenol dosing, the phosgene dosing was continued for another 3 minutes.

Finally, the reactor was stirred for another 15 minutes at pH=4.

In this manner a solution of phenyl chloroformate in methylene chloride was obtained having a phenol content of 4734 ppm and a diphenyl carbonate content of 3873 ppm. The use of such a solution as a chain stopper in a standard polycarbonate preparation yielded a product having a diphenyl carbonate content of only 46 ppm.

EXAMPLE 2

Paracumyl phenylchloroformiate was prepared in a stirred reactor at a temperature which was kept between 3° and 5° C. by cooling. 1320 ml of methylene chloride were provided in the reactor with 150 ml of water. 3.6 g/minute of phosgene were dosed for 10 minutes. 133 g of paracumyl phenol in 332.5 ml of methylene chloride were then dosed in the course of 35 minutes. During the said dosing of paracumyl phenol, 3.6 g/minute of phosgene were added. The pH was kept at a value of 4–6 by dosing with sodium hydroxide solution. During the dosing of paracumyl phenol, 30 ml of water were added once to the reactor. After termination of the dosing of paracumyl phenol, the phosgene dosing was continued for another 2 minutes.

The reactor was finally stirred for another 15 miniutes at pH=4.

In this manner a solution of paracumyl phenyl chloroformiate in methylene chloride was obtained having a content of diparacumyl phenyl carbonate of 2,500 ppm. The use of such a solution as a chain stopper in a standard polycarbonate yielded a product having a content of diparacumyl phenyl carbonate of only 35 ppm.

We claim:

1. A method of preparing an aromatic polycarbonate comprising preparing a compound of formula 1

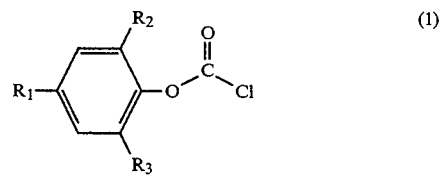

by continuously supplying to a solution of phosgene in a solvent a compound of formula 2

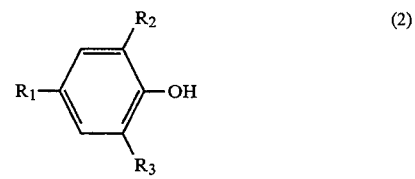

wherein $R_1$, $R_2$ and $R_3$ in formulas 1 and 2 are each independently of H, a branched or non-branched, substituted or unsubstituted alkyl group, or an unsubstituted or substituted aryl group and phosgene in an amount whereby the molar ratio of phosgene to the compound of formula 2 is from 1.5:1 to 3:1 in which solvent the compound of formula 2 reacts with phosgene at a temperature maintained between 0° and 15° C. and a pH between 1 and 6, removing the compound of formula 1 containing no more than 0.5% by weight of dimeric compounds from the solvent; and reacting a carbonate precursor with a diphenol in the presence of the compound of formula 1.

2. A method of preparing an aromatic polycarbonate comprising preparing a compound of formula 1

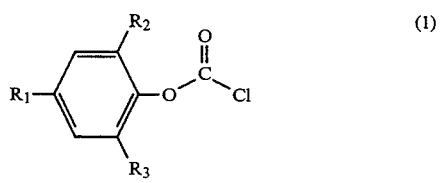

by continuously supplying to a solution of phosgene in a solvent a compound of formula 2

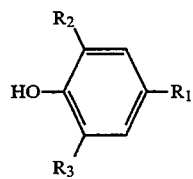 (2)

wherein $R_1$, $R_2$ and $R_3$ in formulas 1 and 2 are each independently H, a branched or non-branched, substituted or unsubstituted alkyl group, or an unsubstituted or substituted aryl group and phosgene in an amount whereby the molar ratio of phosgene to the compound of formula 2 is from 1.5:1 to 3:1 in which solvent the compound of formula 2 reacts with phosgene at a temperature maintained between 0° and 15° C. and a pH between 1 and 6; and reacting a carbonate precursor with a diphenol in the presence of a solution of the compound of formula 1 having a content of diaryl carbonate lower than 5,000 ppm.

3. The method of claim 1 wherein the solvent is dichloromethane or monochlorobenzene.

4. The method of claim 2 wherein the solvent is dichloromethane.

5. The method of claim 1 wherein the compound of formula 1 is phenol and the pH is between 1 and 4.

6. The method of claim 1 wherein the compound of formula 1 is paracumyl phenol and the pH is between 4 and 6.

7. The method of claim 2 wherein the compound of formula 1 is phenol and the pH is between 1 and 4.

8. The method of claim 2 wherein the compound of formula 1 is paracumyl phenol and the pH is between 4 and 6.

* * * * *